(12) United States Patent
Gaska et al.

(10) Patent No.: US 8,980,178 B2
(45) Date of Patent: Mar. 17, 2015

(54) MEDIUM TREATMENT USING ULTRAVIOLET LIGHT

(75) Inventors: Remigijus Gaska, Columbia, SC (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 434 days.

(21) Appl. No.: 12/783,720

(22) Filed: May 20, 2010

(65) Prior Publication Data

US 2010/0296971 A1 Nov. 25, 2010

Related U.S. Application Data

(60) Provisional application No. 61/216,948, filed on May 23, 2009.

(51) Int. Cl.
*G01N 21/00* (2006.01)
*G01N 31/00* (2006.01)
*G01N 33/00* (2006.01)
*C02F 1/32* (2006.01)
(Continued)

(52) U.S. Cl.
CPC . *C02F 1/325* (2013.01); *A61L 2/10* (2013.01); *B01D 46/0043* (2013.01); *B01D 46/10* (2013.01); *C02F 1/30* (2013.01); *C02F 1/32* (2013.01); *A61L 9/20* (2013.01); *B01D 2259/804* (2013.01); *B01D 2273/30* (2013.01); *C02F 1/50* (2013.01); *C02F 1/722* (2013.01); *C02F 2201/003* (2013.01); *C02F 2201/009* (2013.01); *C02F 2201/322* (2013.01); *C02F 2201/3222* (2013.01); *C02F 2201/3226* (2013.01); *C02F 2201/326* (2013.01); *C02F 2209/006* (2013.01); *C02F 2209/40* (2013.01); *C02F 2301/08* (2013.01); *C02F 2303/04* (2013.01)

USPC .................................. 422/62; 422/24

(58) Field of Classification Search
CPC ............. C02F 1/32; C02F 1/30; C02F 1/325; C02F 2201/3222; C02F 2201/3226; A61L 2/10; A61L 9/20
USPC ....................... 422/62, 88, 101, 121, 500, 24; 210/198.1; 96/224
See application file for complete search history.

(56) References Cited

U.S. PATENT DOCUMENTS 3,817,703 A 6/1974 Atwood
4,445,858 A 5/1984 Johnson
(Continued)

OTHER PUBLICATIONS

Elasri et al., "Study of the Response of a Biofilm Bacterial Community to UV Radiation", Appl Environ Microbiaol., May 1999, 65(5), pp. 2025-2031.
(Continued)

*Primary Examiner* — Bobby Ramdhanie
*Assistant Examiner* — Bryan Kilpatrick
(74) *Attorney, Agent, or Firm* — LaBatt, LLC

(57) ABSTRACT

A system for treating a medium, such as water, with ultraviolet light is provided. The system can include an ultraviolet treatment chamber that is shaped to reduce reflections of the ultraviolet light within the ultraviolet treatment chamber and/or improve absorption of the ultraviolet light by the medium. Furthermore, the system can add an agent to the medium within the treatment chamber to further treat one or more contaminants that may be present within the medium. Still further, additional treatment, such as filtering the medium with a permeable material can be implemented within the treatment system.

20 Claims, 5 Drawing Sheets

(51) Int. Cl.
*A61L 2/10* (2006.01)
*B01D 46/00* (2006.01)
*B01D 46/10* (2006.01)
A61L 2/00 (2006.01)
C02F 1/30 (2006.01)
A61L 9/20 (2006.01)
C02F 1/50 (2006.01)
C02F 1/72 (2006.01)

(56) References Cited

U.S. PATENT DOCUMENTS

| | | | |
|---|---|---|---|
| 4,501,969 A | 2/1985 | Lymneos | |
| 5,364,645 A | 11/1994 | Lagunas-Solar et al. | |
| 5,919,422 A | 7/1999 | Yamanaka et al. | |
| 6,565,803 B1 | 5/2003 | Bolton et al. | |
| 6,576,188 B1 | 6/2003 | Rose et al. | |
| 6,579,495 B1 | 6/2003 | Maiden | |
| 6,673,137 B1 | 1/2004 | Wen | |
| 6,818,177 B1 | 11/2004 | Turcotte | |
| 6,919,019 B2* | 7/2005 | Baca et al. | 210/97 |
| 7,091,495 B2* | 8/2006 | Panico et al. | 250/432 R |
| 7,160,370 B2 | 1/2007 | Baca et al. | |
| 2002/0074559 A1 | 6/2002 | Dowling et al. | |
| 2002/0176809 A1 | 11/2002 | Siess | |
| 2003/0194692 A1 | 10/2003 | Purdum | |
| 2007/0196235 A1 | 8/2007 | Shur et al. | |
| 2008/0203004 A1* | 8/2008 | Abe et al. | 210/205 |

OTHER PUBLICATIONS

Shur et al., "Deep-Ultraviolet Light-Emitting Diodes", IEEE Transactions on Electron Devices, vol. 57, No. 1, Jan. 2010, pp. 12-25.

PTO Office Action, U.S. Appl. No. 11/380,512, Notification Date Oct. 2, 2008, 10 pages.

PTO Notice of Allowance, U.S. Appl. No. 11/380,512, Date Mailed Feb. 27, 2009.

* cited by examiner

MEDIUM TREATMENT USING ULTRAVIOLET LIGHT

REFERENCE TO PRIOR APPLICATIONS

The current application claims the benefit of U.S. Provisional Application No. 61/216,948, titled "Flow sterilization system", which was filed on 23 May 2009, and which is hereby incorporated by reference.

TECHNICAL FIELD

The disclosure relates generally to treating a medium, and more particularly, to treating a medium using ultraviolet radiation.

BACKGROUND ART

Ultraviolet radiation has been successfully used in the purification (e.g., sterilization) of various media, such as air, water, and food. In general, it is desirable that the ultraviolet radiation comprises wavelength(s) that are close to the absorption peak(s) of biologically significant molecules of DNA and/or proteins of a target impurity. For example, impurities, such as a bacterium, a virus, a protozoan, a germ, etc., comprise DNA/proteins having corresponding absorption peaks. By exposing the DNA/proteins to ultraviolet radiation having a wavelength close to the absorption peak(s) for a sufficient time and at a sufficient power, the impurity is destroyed. To this extent, exposing a medium that includes one or more of these impurities to sufficient ultraviolet radiation can destroy some or all of the impurities. When sufficient impurities are destroyed, the medium is purified to a safe condition.

Various approaches have incorporated different sources for the ultraviolet radiation. To this extent, previous approaches have proposed the use of a mercury lamp, an ultraviolet diode, and/or an ultraviolet laser diode for generating the ultraviolet radiation. Additionally, various approaches have proposed the use of mirrors, a serpentine path, and/or many ultraviolet radiation sources disposed throughout a region to help ensure that a sufficient amount of ultraviolet radiation is provided throughout an area including a flowing medium.

SUMMARY OF THE INVENTION

Aspects of the invention provide a solution for treating a medium, such as water, with ultraviolet light. The solution can include an ultraviolet treatment chamber that is shaped to reduce reflections of the ultraviolet light within the ultraviolet treatment chamber and/or improve absorption of the ultraviolet light by the medium. Furthermore, the solution can include adding an agent to the medium within the treatment chamber to further treat one or more contaminants that may be present within the medium. Still further, additional treatment, such as filtering the medium with a permeable material can be implemented by the treatment solution.

A first aspect of the invention provides a system for treating a medium, the system comprising: a first ultraviolet source; and a shaped treatment chamber, wherein the shaped treatment chamber includes: a first portion from which ultraviolet light emitted by the first ultraviolet source enters the shaped treatment chamber; and a second portion fluidly attached to the first portion, wherein an area of a cross-section of the second portion increases with distance from the first portion to approximately conform to at least one of: a space emission pattern of the first ultraviolet source or a flow absorption distance dependence from the first ultraviolet source.

A second aspect of the invention provides a system for treating a medium, the system comprising: an ultraviolet treatment chamber through which the medium moves; an ultraviolet source, wherein the ultraviolet source emits ultraviolet light into the ultraviolet treatment chamber; an agent source, wherein the agent source introduces an agent for treating the medium within the ultraviolet treatment chamber; and a computer system configured to implement a method of treating the medium by: determining at least one of: a level of contamination of the medium or a type of contamination of the medium; and operating the ultraviolet source and the agent source based on the at least one of: the level of contamination of the medium or the type of contamination of the medium.

A third aspect of the invention provides a system for treating a medium, the system comprising: an ultraviolet treatment chamber; an ultraviolet source, wherein the ultraviolet source emits ultraviolet light into the ultraviolet treatment chamber; an outer treatment chamber encapsulating the ultraviolet treatment chamber, wherein the medium first enters the outer treatment chamber and wherein at least a portion of at least one wall of the ultraviolet treatment chamber is permeable to allow the medium to pass there through into the ultraviolet treatment chamber; and an outlet located within the ultraviolet treatment chamber, wherein the medium exits the ultraviolet treatment chamber and the outer treatment chamber via the outlet.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for treating a medium, such as water, with ultraviolet light. The solution can include an ultraviolet treatment chamber that is shaped to reduce reflections of the ultraviolet light within the ultraviolet treatment chamber and/or improve absorption of the ultraviolet light by the medium. Furthermore, the solution can include adding an agent to the medium within the treatment chamber to further treat one or more contaminants that may be present within the medium. Still further, additional treatment, such as filtering the medium with a permeable material can be implemented by the treatment solution. As used herein, unless otherwise noted, the term "set" means one or more (i.e., at least one) and the phrase "any solution" means any now known or later developed solution.

Figure 1:
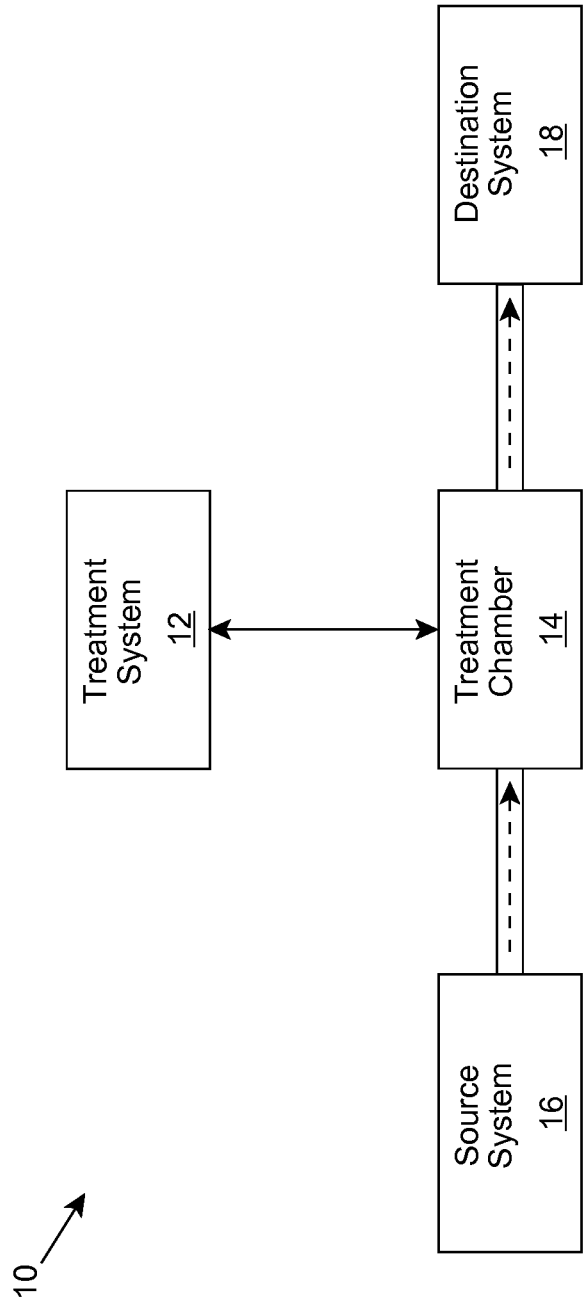
FIG. 1 shows an illustrative environment for treating a medium according to an embodiment.

Turning to the drawings, FIG. 1 shows an illustrative environment 10 for treating a medium according to an embodiment. To this extent, environment 10 includes a treatment system 12 that can perform a process described herein in order to treat (e.g., purify) a medium moving through a treatment chamber 14 in environment 10 using ultraviolet radiation. In general, environment 10 includes a source system 16, which provides a source of the medium from which the medium will enter treatment chamber 14, and a destination system 18, which receives the medium after it exits treatment chamber 14. Depending on the particular type of medium and/or application for an implementation of environment 10, destination system 18 can perform further processing of the medium, the medium can exit environment 10 via destination system 18, and/or the like.

The medium can comprise any type of medium for which treatment, such as purification, using ultraviolet radiation is desired. The medium can comprise any form, such as a liquid, a gas, or one or more solids. In an embodiment, the medium comprises a liquid. In a more particular embodiment, the liquid comprises water. However, it is understood that the medium can comprise other types of liquid, such as a biological fluid, and/or the like. In another embodiment, the medium comprises a granular substance, such as food products.

Environment 10 can be applied to various types of applications. For example, environment 10 can be implemented as part of a refrigerator or other home appliance. For example, the medium can comprise water that is dispensed from the refrigerator via destination system 18, e.g., for human consumption. In this case, water obtained from source system 16 (e.g., via a waterline and/or storage tank within the refrigerator) can be treated within treatment chamber 14 prior to being dispensed. In another illustrative application, environment 10 can be implemented within a desalination system. In this case, subsequent to and/or prior to desalination (e.g., by source system 16 or destination system 18, respectively), the water can be passed through treatment chamber 14 for purification. In still another illustrative application, environment 10 can be implemented as part of a dialysis treatment system. For example, blood can be removed from a patient via source system 16, and subsequent to and/or prior to the removal of uric acid and/or urea (e.g., by source system 16 or destination system 18, respectively), the blood can be passed through treatment chamber 14 for purification before being reintroduced into the patient via destination system 18.

Figure 2:
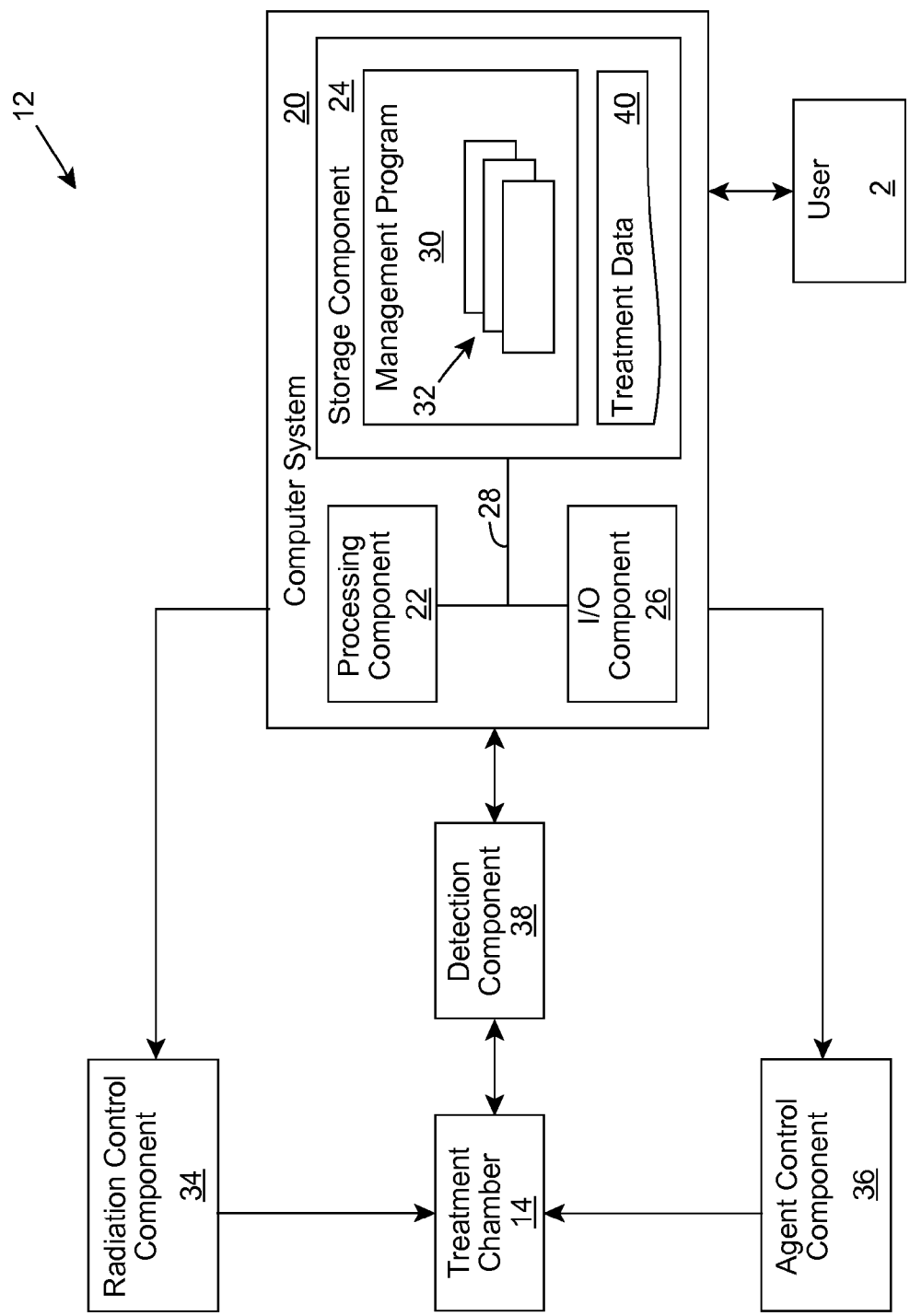
FIG. 2 shows an illustrative treatment system according to an embodiment.

FIG. 2 shows an illustrative treatment system 12 according to an embodiment. As illustrated, treatment system 12 includes a computer system 20, which is configured to manage treatment of a medium within treatment chamber 14 by performing a process described herein. In particular, computer system 20 is shown including a management program 30, which makes computer system 20 operable to manage treatment of the medium by performing a process described herein.

Computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as management program 30, which is at least partially fixed in storage component 24. While executing program code, processing component 22 can process data, which can result in reading and/or writing transformed data from/to storage component 24 and/or I/O component 26 for further processing. Pathway 28 provides a communications link between each of the components in computer system 20. I/O component 26 can comprise one or more human I/O devices, which enable a human user 2 to interact with computer system 20 and/or one or more communications devices to enable a system user 2 to communicate with computer system 20 using any type of communications link. To this extent, management program 30 can manage a set of interfaces (e.g., graphical user interface(s), application program interface, and/or the like) that enable human and/or system users 2 to interact with management program 30. Further, management program 30 can manage (e.g., store, retrieve, create, manipulate, organize, present, etc.) the data, such as treatment data 40, using any solution.

In any event, computer system 20 can comprise one or more general purpose computing articles of manufacture (e.g., computing devices) capable of executing program code, such as management program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, management program 30 can be embodied as any combination of system software and/or application software.

Furthermore, management program 30 can be implemented using a set of modules 32. In this case, a module 32 can enable computer system 20 to perform a set of tasks used by management program 30, and can be separately developed and/or implemented apart from other portions of management program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Additionally, it is understood that some of the functionality discussed herein may not be implemented or additional functionality may be included as part of computer system 20.

When computer system 20 comprises multiple computing devices, each computing device can have only a portion of management program 30 fixed thereon (e.g., one or more modules 32). However, it is understood that computer system 20 and management program 30 are only representative of various possible equivalent computer systems that may perform a process described herein. To this extent, in other embodiments, the functionality provided by computer system 20 and management program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 20 includes multiple computing devices, the computing devices can communicate over any type of communications link. Further, while performing a process described herein, computer system 20 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, management program 30 enables computer system 20 to manage treatment (e.g., purification) of a medium. To this extent, computer system 20 can operate one or more components 34, 36, 38, each of which can perform a treatment-related action with respect to the medium within treatment chamber 14. For example, computer system 20 can manage operation of a radiation control component 34, which can operate one or more ultraviolet sources, each of which is configured to emit ultraviolet radiation that is directed to shine within treatment chamber 14. Similarly, computer system 20 can manage operation of an agent control component 36, which can operate one or more sources of agents (e.g., a germicide) to selectively release an agent within treatment chamber 14. Still further, computer system 20 can manage operation of a detection component 38, which can include one or more sensing devices for detecting one or more attributes of the medium moving through treatment chamber 14, e.g., to determine a level of contamination of the medium.

As discussed herein, computer system 20 can manage treatment data 40 using any solution, which computer system 20 can use to operate components 34, 36, 38. Computer system 20 can obtain any combination of one or more of various types of treatment data 40 from detection component 38. While not shown for clarity, computer system 20 also can obtain some or all of the treatment data 40 from source system 16 (FIG. 1) and/or destination system 18 (FIG. 1). For example, source system 16 and/or destination system 18 can include a flow control device, such as a pump, valve, and/or the like, which controls the volume and/or rate of flow of the medium through treatment chamber 14. Computer system 20 can obtain treatment data 40 on the operation of the flow control device(s) and use the data when operating the various components 34, 36, 38 (e.g., activating/deactivating some or all of the devices of a component). Additionally, source system 16, destination system 18, and/or detection component 38 can include one or more sensing devices, which detect one or more attributes of the medium moving through the environment 10. For example, illustrative sensing devices include sensing devices for detecting a flow rate, a volume of flow, a level of contamination, and/or the like. Computer system 20 can obtain treatment data 40 corresponding to the attribute(s) of the medium and use it to operate the various components 34, 36, 38.

In any event, radiation control component 34 can comprise one or more ultraviolet sources, such as one or more of: a set of mercury lamps, a set of ultraviolet light emitting diodes, and/or a set of ultraviolet laser diodes. Ultraviolet light emitted by the set of ultraviolet sources can be directed into treatment chamber 14 using any solution. For example, in an embodiment, one or more of the ultraviolet sources is located such that the ultraviolet light shines within treatment chamber 14. The ultraviolet source(s) can be located on an interior of a wall forming treatment chamber 14. Additionally, one or more ultraviolet sources can be located apart from treatment chamber 14, and at least a portion of the ultraviolet light emitted by the ultraviolet source(s) can be directed to the interior of treatment chamber 14 using a waveguide structure (e.g., optical fibers). Still further, a waveguide structure can be included to direct a portion of the ultraviolet light emitted by an ultraviolet source within the treatment chamber 14 to emanate from another location within the treatment chamber 14. In an embodiment, one or more walls of the treatment chamber 14 include a waveguide structure (e.g., optical fibers embedded therein) to deliver the ultraviolet light to desired locations within the treatment chamber 14.

Radiation control component 34 can include a set of ultraviolet sources that are selected to emit a particular set of wavelengths of ultraviolet light with a corresponding power (e.g., ultraviolet light of a particular spectral power distribution) based on a particular implementation of the treatment system 12. For example, the set of ultraviolet sources can be selected based on the medium, a set of anticipated attributes of the medium, a desired treatment, and/or the like, for the corresponding application. To this extent, based on an anticipated (e.g., maximum) volume, flow rate, and/or contamination level of the medium, radiation control component 34 can be configured to include a sufficient number of ultraviolet sources to deliver a dose of ultraviolet light that is sufficient to perform a desired treatment of the medium while it passes through treatment chamber 14. The required dose of ultraviolet light also can vary based on the desired treatment. For example, a higher dose of radiation may be required to purify (e.g., sterilize) the medium, as compared to a dose of radiation required to maintain a level of contamination below a specified acceptable level, suppress (e.g., prevent) bacterial or mold growth in the medium, and/or the like.

The set of wavelengths emitted by the ultraviolet sources can be selected to correspond to the desired treatment and/or types of contaminants anticipated to be found in the medium. For example, for contaminants comprising DNA (e.g., mold, bacteria, and/or the like), the set of wavelengths can include ultraviolet wavelengths that destroy the DNA. In an embodiment, the ultraviolet wavelengths are between approximately 250-280 nanometers. Additionally, the ultraviolet radiation can be used to activate an agent to perform a desired treatment. For example, treatment system 12 can introduce an agent into treatment chamber 14 and activate the agent using ultraviolet light generated by radiation control component 34. In an embodiment, treatment system 12 introduces hydrogen peroxide ($H_2O_2$) into treatment chamber 14 and activates the hydrogen peroxide with ultraviolet radiation having wavelengths below 250 nanometers. In this case, the activated hydrogen peroxide can facilitate the destruction of various chemical contaminants in addition to the destruction of the chemical contaminants due to photolysis. In an illustrative application, radiation control component 34 can include two or more sets of ultraviolet sources, each of which is configured to emit ultraviolet light of a distinct set of wavelengths for different treatment operations, such as the concurrent destruction of both DNA and chemical contaminants, destruction of different types of DNA, and/or the like. In this case, computer system 20 can independently operate the set of the sets of ultraviolet sources based on detected contaminant(s) in the medium and/or desired treatment operation(s).

Agent control component 36 can include one or more of various types of agents, which can be selected based on the application for a particular implementation of treatment system 12. For example, as discussed above, agent control component 36 can include hydrogen peroxide, which agent control component 36 can selectively release into treatment chamber 14 based on an anticipated/detected presence of a chemical contaminant in the medium. Similarly, agent control component 36 can include one or more types of germicides, which agent control component 36 can selectively release into treatment chamber 14 based on an anticipated/detected presence of a biological contaminant in the medium. In either case, an amount of the agent released into the treatment chamber 14 can be adjusted based on a volume/flow of the medium, a level of the contamination, and/or the like.

The delivery of the agent(s) into treatment chamber 14 can be performed in such a manner to enable a thorough mixing of the agent with the medium moving through the treatment chamber 14. To this extent, agent control component 36 and/or treatment chamber 14 can be configured to deliver the agent(s) in a manner that facilitates thorough mixing with the medium. For example, similar to the waveguide structure discussed herein, treatment chamber 14 can comprise structures (e.g., passageways) configured to enable delivery of the agent(s) to one or more desired locations within the treatment chamber 14. Furthermore, one or more locations within treatment chamber 14 corresponding to an area of turbulence for the medium can be selected for delivering the agent, thereby facilitating mixing the agent with the medium. Additionally, agent control component 36 can add the agent(s) to the medium prior to/concurrent with the medium entering the treatment chamber 14.

Detection component 38 can include one or more sensing elements for detecting one or more attributes of the medium moving through treatment chamber 14. The sensing element(s) of detection component 38 can be configured to sense attribute(s) of medium as it passes any location with respect to treatment chamber 14, e.g., before and/or after treatment chamber 14, at the inlet and/or outlet of treatment chamber 14, within a central area of treatment chamber 14, and/or the like. The sensing element(s) of detection component 38 can be selected to sense any of various attributes of the medium based on an application for a particular implementation of treatment system 12. In an embodiment, detection component 38 includes one or more sensing elements to detect a speed, volume, and/or the like, of the medium.

Additionally, detection component 38 can include one or more sensing elements to detect attributes that are associated with a contamination type and level of the medium. For example, detection component 38 can include one or more chemical sensors for measuring a level of a corresponding chemical contaminant in the medium. Similarly, detection component 38 can include one or more biological sensors for measuring a level of a biological contaminant in the medium.

In an embodiment, detection component 38 can include a set of emitting elements that operate in conjunction with a set of sensing elements to detect attribute(s) of the medium. For example, detection component 38 can include a set of ultraviolet sources, which emit ultraviolet light directed at the medium and a corresponding set of ultraviolet sensors, which detect a reflection of the ultraviolet light from the medium. In this case, computer system 20 can process the detected ultraviolet light to determine a fluorescence of the medium, which computer system 20 can correlate with a contamination type and/or level of the medium. For example, computer system 20 can compare a spectrum of the fluorescence of the medium under excitation by ultraviolet light of a particular peak wavelength with the known fluorescence spectra of various contaminants under excitation by ultraviolet light of the peak wavelength to determine whether any of the contaminants is present in the medium. Furthermore, computer system 20 can measure a phase shift of a fluorescent signal to determine whether one or more types of contaminants is present. Similarly, computer system 20 can determine and evaluate an intensity of the fluorescence to determine a degree of the contamination.

Computer system 20 can adjust the operation of radiation control component 34 and/or agent control component 36 in response to the attribute(s) of medium detected by detection component 38. For example, computer system 20 can implement a feedback control loop. In this case, computer system 20 can adjust the dose, spectral power distribution, and/or output power of ultraviolet radiation delivered by radiation control component 34, the concentration and/or type of agent delivered by agent control component 36, and/or the like, to maintain a desired level of contamination, bacterial/mold growth, and/or the like, relative to (e.g., below) a specified level as detected using detection component 38. In an embodiment, radiation control component 34 includes multiple ultraviolet sources, each of which emits ultraviolet light of a differing wavelength. Computer system 20 can selectively operate one or more of the ultraviolet sources based on a desired wavelength and/or dose. Computer system 20 can determine the desired wavelength and/or dose based on the absorption characteristics of a contaminant and/or the level of contamination present in the medium.

Furthermore, computer system 20 can adjust the operation of one or more flow control devices, such as a pump, valve, and/or the like, e.g., implemented in source system 16 (FIG. 1) and/or destination system 18 (FIG. 1), to adjust the volume and/or flow rate of the medium moving through treatment chamber 14 based on the level of contamination. To this extent, computer system 20 can slow/reduce an amount of the medium flowing through treatment chamber 14 in order to enable a longer duration/higher concentration of a desired treatment on the medium. Similarly, computer system 20 can speed up/increase an amount of the medium flowing through treatment chamber 14 when the detected level of contamination is below the desired level of contamination.

Additionally, computer system 20 can operate one or more flow control devices to stir the flow of the medium and/or otherwise ensure a more uniform exposure of the treatment (e.g., ultraviolet radiation and/or agent) with the medium. For example, computer system 20 can relatively rapidly vary the volume/rate of flow (e.g., pulse the flow) to increase turbulence within treatment chamber 14. Additionally, treatment chamber 14 can include one or more mechanical mixing devices, which can be operated by computer system 20. Still further, treatment chamber 14 can include one or more fixed components, such as barriers, or the like, which can passively act on the flow of the medium to increase turbulence within the treatment chamber 14.

Treatment chamber 14 can include one or more additional features, which increase the efficacy of the ultraviolet and/or agent-based treatment of the medium. For example, at least a portion of the internal walls of treatment chamber 14 can be coated with an agent, such as a germicidal agent, to suppress growth of a possible contaminant of the medium within the treatment chamber 14. Additionally, a reflectivity of the internal walls of the treatment chamber 14 can be configured to improve the re-absorption of the ultraviolet light in the flow of the medium. For example, the internal walls can be configured to be highly reflective of ultraviolet light. To this extent, the internal walls can be covered with aluminum, or the like, which will reflect substantially all of the ultraviolet light.

Similarly, the directional reflectivity of the internal walls can be configured to improve re-absorption of the ultraviolet light. Such reflectivity can be changed as a function of the distance from an ultraviolet source. For example, the varying directional reflectivity can be configured to scatter the ultraviolet light, direct the ultraviolet light to a particular area within the chamber, and/or the like. In an embodiment, the internal walls closer to the ultraviolet source are configured to increase scattering of the ultraviolet light more than the internal walls farther from the ultraviolet source, where less ultraviolet light will be present. In another embodiment, the internal walls closer to the ultraviolet source are configured to direct a substantial portion of the ultraviolet light impinging thereon further away from the ultraviolet source. The reflectivity of the walls can be altered using any solution, e.g., by varying attributes of a reflective coating applied to the walls, patterning the walls (e.g., with grooves or the like) with a variable profile, and/or the like.

Figure 3:
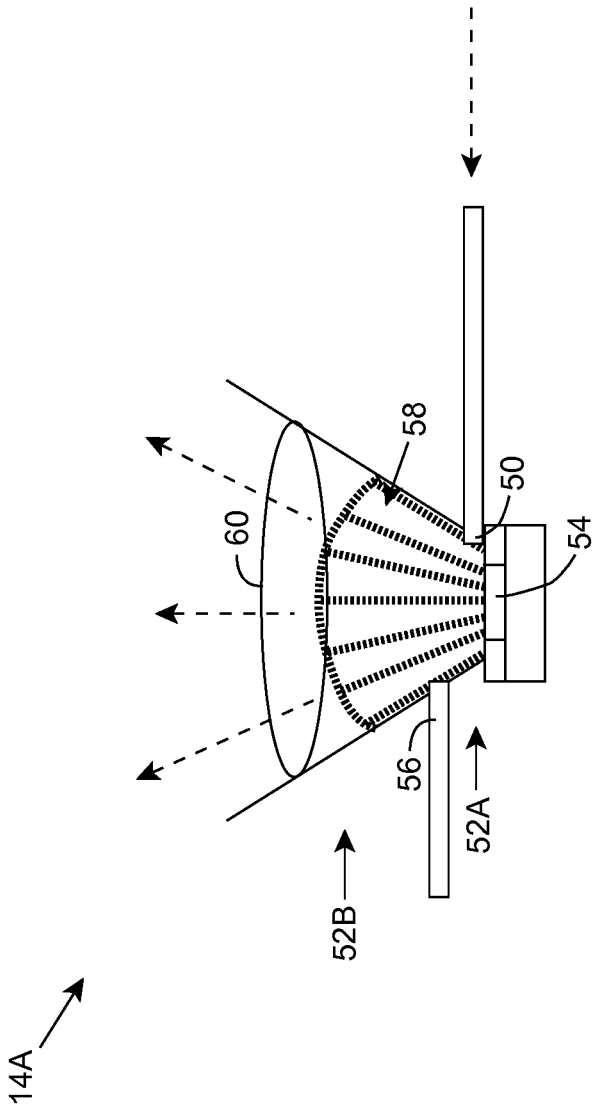
FIG. 3 shows a portion of an illustrative treatment chamber according to an embodiment.

Furthermore, FIG. 3 shows a portion of an illustrative treatment chamber 14A according to an embodiment. As illustrated, treatment chamber 14A includes an inlet 50 located adjacent to a first portion 52A of the treatment chamber 14A. The medium enters the treatment chamber 14A through the inlet 50 and subsequently flows in an approximately perpendicular direction from the inlet 50 through the treatment chamber 14A. In this manner, an amount of mixing of the medium within treatment chamber 14A is increased over the amount of mixing that would occur when the medium is allowed to move straight through treatment chamber 14A.

Additionally, treatment chamber 14A includes an ultraviolet source 54 for delivering ultraviolet light into the interior of treatment chamber 14A and an agent source 56 for delivering an agent into the interior of treatment chamber 14A. Agent source 56 can be located to introduce the agent(s) into treatment chamber 14A at a location of treatment chamber 14A where the flow of the medium is turbulent, e.g., adjacent to an interior wall of treatment chamber 14A opposite the location of inlet 50. Furthermore, ultraviolet source 54 can be located to enable delivery of a desired dose of ultraviolet radiation 58 to substantially all of the medium moving through treatment chamber 14A.

In an embodiment, ultraviolet source 54 is located adjacent to the first portion 52A of treatment chamber 14A, and emits ultraviolet light 58 into the shaped treatment chamber 14A directed towards a second portion 52B of treatment chamber 14A, which is fluidly attached to the first portion 52A. Second portion 52B of treatment chamber 14A comprises a shape that is configured to reduce reflections of the ultraviolet light 58 off of the internal walls of treatment chamber 14A, thereby reducing any loss in intensity of the ultraviolet light 58 caused by the reflections. As illustrated, second portion 52B can comprise a cone shape, in which an area of a cross-section 60 of the cone increases with the distance of the cross-section 60 from the first portion 52A and the corresponding ultraviolet source 54.

The shape of the cone (e.g., the cone angle) can be configured to increase the efficacy with which the ultraviolet light 58 can treat the medium. For example, second portion 52B can comprise a cone shape having a cone angle configured to approximately conform to a space emission pattern of the ultraviolet source 54, e.g., by matching the angular distribution of the intensity of ultraviolet light 58 emitted by ultraviolet source 54. The space emission pattern of a particular ultraviolet source 54 can vary based on various attributes of the ultraviolet source 54, and can be determined by acquiring various measurements of the intensity of the ultraviolet light from different angles around the ultraviolet source 54. The cone angle can be configured to contain the main lobe of intensity of the ultraviolet light emitted by the ultraviolet source 54. The main lobe of intensity can range between narrowly focused (e.g., an approximately 20 degree beam angle or less) to widely focused (e.g., an approximately 100 degree beam angle or greater).

Similarly, the shape of the cone can be configured to approximately conform to a flow absorption distance dependence from the ultraviolet source 54 of the medium. For example, an absorption coefficient for a particular medium can be determined based on the wavelength(s) of the ultraviolet light emitted by the ultraviolet source 54, and a corresponding distance from the ultraviolet source 54 at which the ultraviolet light is completely absorbed by the medium can be determined. One or more dimensions of the cone shape can be configured based on the distance. For example, the total distance that the cone shape extends away from the ultraviolet source 54 can be selected to approximate the distance, after which point the cone shape is not required.

Figure 4:
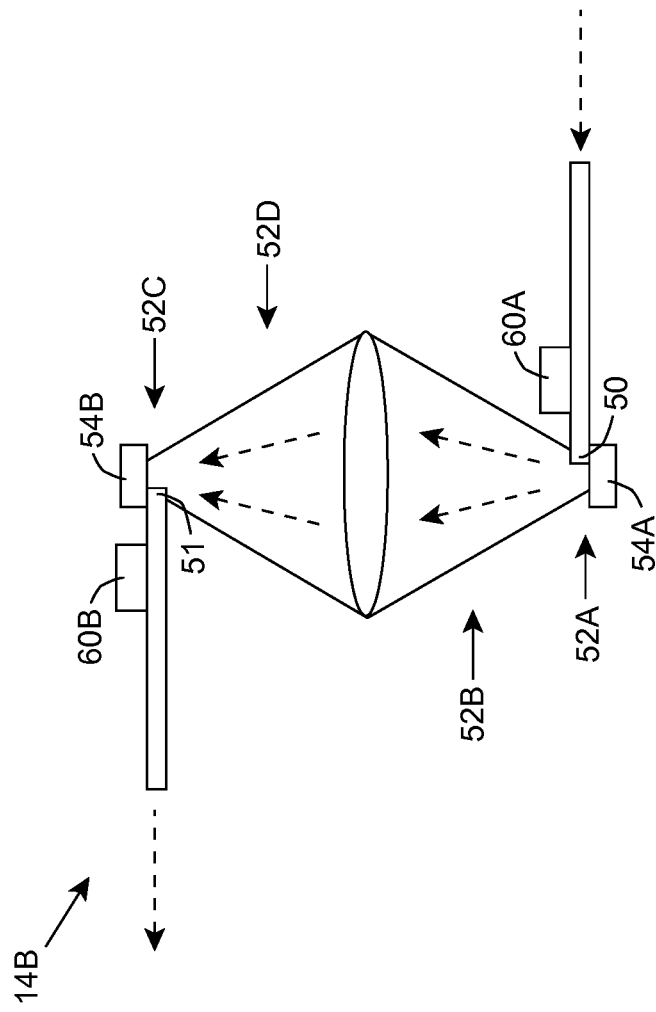
FIG. 4 shows an illustrative treatment chamber according to an embodiment

FIG. 4 shows an illustrative treatment chamber 14B according to an embodiment. As illustrated, the internal area of treatment chamber 14B comprises a double cone shape, where the wide ends of the respective cones form the central region of the treatment chamber 14B. To this extent, treatment chamber 14B includes two narrow portions 52A, 52C from which ultraviolet light is directed into the treatment chamber from corresponding ultraviolet sources 54A, 54B, respectively. Additionally, treatment chamber 14B includes two portions 52B, 52D that are fluidly attached to one another and the corresponding narrow portions 52A, 52C, respectively, which form the double cone shape of the interior. Each portion 52B, 52D can comprise a cone shape having dimensions determined as described herein. For example, the cone angle can be configured to contain the main lobe of intensity of the ultraviolet light emitted by the corresponding ultraviolet source, and the extent of each portion 52B, 52D can be configured to approximate the distance from the corresponding ultraviolet source 54A, 54B at which the ultraviolet light is completely absorbed by the medium.

As illustrated, the medium can enter the treatment chamber 14B through an inlet 50 located adjacent to narrow portion 52A, and exit the treatment chamber 14B through an outlet 51 located adjacent to narrow portion 52C. In this configuration, the flow of the medium is generally away from ultraviolet source 54A and towards ultraviolet source 54B. Ultraviolet sources 54A, 54B can emit similar ultraviolet light or different ultraviolet light. In the latter case, ultraviolet source 54A can emit ultraviolet light for performing a first treatment (e.g., activate an agent), while ultraviolet source 54B emits ultraviolet light for performing a second, distinct treatment (e.g., destruction of DNA).

Computer system 20 (FIG. 2) can operate ultraviolet sources 54A, 54B together or independent from one another. To this extent, computer system 20 can obtain a contamination information (e.g., a degree of contamination, a type of contamination, and/or the like) from a detection element 60A located proximate to inlet 50. Based on the contamination information, computer system 20 can operate one or both ultraviolet sources 54A, 54B. For example, when detection element 60A indicates little or no contamination of the medium, computer system 20 can turn/leave ultraviolet sources 54A, 54B off, or cause one or both ultraviolet sources 54A, 54B to deliver a relatively low dose of ultraviolet light to suppress any potential growth of contaminants. However, when detection element 60A indicates a relatively high amount of contamination of the medium, computer system 20 can operate ultraviolet sources 54A, 54B to deliver a relatively high dose of ultraviolet light, e.g., to harm the DNA of the contaminants present, activate an agent introduced into the flow of the medium (e.g., by computer system 20 operating an agent source 56 (FIG. 3)), and/or the like. Similarly, computer system 20 can adjust the wavelength of ultraviolet light emitted from one or both ultraviolet sources 54A, 54B based on the type of contamination.

Furthermore, treatment chamber 14B can include a detection element 60B located proximate to outlet 51. Computer system 20 can adjust the operation of the ultraviolet sources 54A, 54B and/or an agent source 56 based on contamination information obtained from detection element 60B. For example, when detection element 60B indicates that a contamination level of the medium remains above a threshold level (e.g., an intermediate level between zero and an acceptable level of contamination), computer system 20 can increase a dose of the ultraviolet light delivered by ultraviolet sources 54A, 54B, e.g., by increasing the intensity of the ultraviolet light emitted by one or both ultraviolet sources 54A, 54B. Similarly, when detection element 60B indicates that the contamination level of the medium is below a threshold level, computer system can decrease the dose of the ultraviolet light delivered by ultraviolet sources 54A, 54B. Computer system 20 can make similar adjustments to an amount of an agent delivered by one or more agent source(s) 56.

Figure 5:
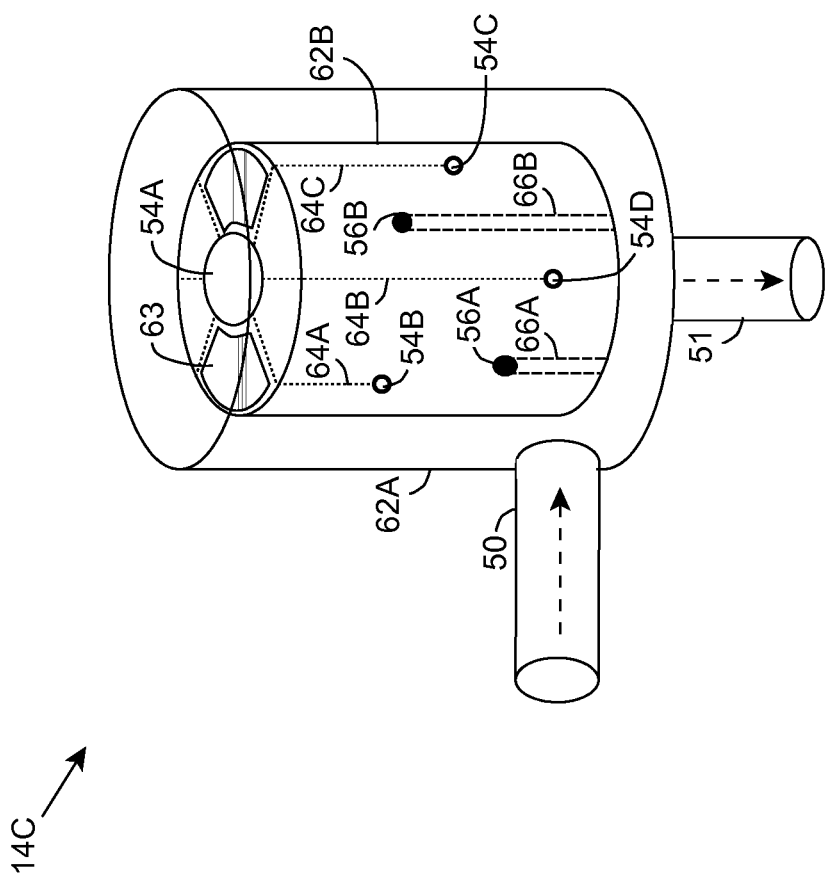
FIG. 5 shows another illustrative treatment chamber according to an embodiment.

An illustrative treatment chamber also can be configured for the removal of large scale contaminants via filtration. To this extent, FIG. 5 shows another illustrative treatment chamber 14C according to an embodiment. Treatment chamber 14C includes an outer treatment casing 62A with an inlet 50, and an inner treatment casing 62B with an outlet 51 located therein. At least a portion of inner treatment casing 62B can be permeable to the medium traveling through treatment chamber 14C. For example, a portion of the inner treatment casing 62B can comprise one or more areas 63 comprising a permeable material, including openings, and/or the like. To this extent, in operation, the medium can enter an outer treatment chamber of treatment chamber 14C via inlet 50, pass through the permeable portion 63 of inner treatment casing 62B to enter an inner treatment chamber of treatment chamber 14C, and exit treatment chamber 14C from the inner treatment chamber via outlet 51. In this manner, any contaminants that are present in medium upon entering via inlet 50 can be removed as the medium passes through the inner treatment casing 62B prior to exiting treatment chamber 14C via outlet 51. While inner treatment casing 62B is shown including only certain areas that are permeable, it is understood that any location(s) or all of inner treatment casing 62B can be permeable to the medium.

Additionally, while within the inner treatment area formed by inner treatment casing 62B, the medium can be further treated with ultraviolet light and/or agent(s). To this extent, inner treatment casing 62B is shown including a plurality of ultraviolet sources 54A-54D. Ultraviolet light can be directed into the inner treatment area from each ultraviolet source 54A-54D using any solution. For example, ultraviolet source 54A can comprise a set of ultraviolet light emitting diodes or the like, which is configured to emit ultraviolet light that is directed into the inner treatment area. Ultraviolet sources 54B-D can direct a portion of the ultraviolet light generated by ultraviolet source 54A to different locations within the inner treatment area via waveguide structures 64A-C located within the inner treatment casing 62B.

Similarly, inner treatment casing 62B can include one or more agent sources 56A, 56B, which can deliver agent(s) into the inner treatment area, e.g., via one or more agent delivery structures 66A, 66B located within the inner treatment casing 62B. It is understood that the various ultraviolet and/or agent sources can be located to deliver a sufficient treatment dose to the medium as it moves through the inner treatment area prior to exiting via the outlet 51. For example, inner treatment casing 62B can be permeable only in a region that is opposite the location of outlet 51, and the various ultraviolet and/or agent sources can be located to treat the medium as it moves from the permeable area to the outlet 51. While an illustrative configuration is shown, it is understood that the invention is not limited to any particular configuration or number of sources. Additionally, it is understood that while cylindrical outer and inner treatment casings 62A, 62B are shown, either treatment casing 62A, 62B can comprise any shape. Still further, it is understood that outer treatment casing 62A can be configured to include agent and/or ultraviolet sources for treating the medium while it is within the outer treatment area before it enters the inner treatment area.

While primarily shown and described herein as a method and system for treating a medium, it is understood that aspects of the invention further provide various alternative embodiments. For example, in one embodiment, the invention provides a computer program fixed in at least one computer-readable medium, which when executed, enables a computer system to implement a method of treating a medium as shown and described herein. To this extent, the computer-readable medium includes program code, such as management program 30 (FIG. 2), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as management program 30 (FIG. 2), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for treating a medium. In this case, a computer system, such as computer system 20 (FIG. 2), can be obtained (e.g., created, maintained, made available, etc.) and one or more components, such as components 34, 36, and 38 of FIG. 2, for performing a process described herein can be obtained (e.g., created, purchased, used, modified, etc.) and deployed along with the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

It is understood that aspects of the invention can be implemented as part of any type of system that performs a process described herein in order to treat a medium. For example, in an illustrative application, the various components/systems of treatment system 12 (FIG. 2) can be implemented as part of a self-contained system that is capable of operating the components of treatment system 12 and/or one or more flow control devices (e.g., a pump) without connection to a power grid. To this extent, the various components can be powered by a power system that generates and stores energy based on one or more ambient conditions of the area in which the treatment system 12 is implemented. For example, the power system can include one or more solar cells, or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system for treating a medium, the system comprising:
a first ultraviolet source; and
a shaped treatment chamber, wherein the shaped treatment chamber defines an interior comprising:
a first portion from which ultraviolet light emitted by the first ultraviolet source enters the shaped treatment chamber; and
a second portion fluidly attached to the first portion, wherein an area of a cross-section of the second portion substantially parallel to the first portion increases with distance from the first portion such that the second portion approximately conforms to at least one of: an unobstructed space emission pattern of the first ultraviolet source or a flow absorption distance dependence from the first ultraviolet source of the medium.

2. The system of claim 1, further comprising an inlet adjacent to the first portion, wherein the medium enters the shaped treatment chamber through the inlet and flows through the second portion away from the first portion.

3. The system of claim 1, further comprising an outlet adjacent to the first portion, wherein the medium flows through the second portion towards the first portion and exits the shaped treatment chamber through the outlet.

4. The system of claim 1, wherein the shaped treatment chamber further includes:
a second ultraviolet source;
a third portion, distinct from the first portion, from which ultraviolet light emitted by the second ultraviolet source enters the shaped treatment chamber; and
a fourth portion fluidly attached to the third portion and the second portion, wherein an area of a cross-section of the fourth portion increases with distance from the third portion to approximately conform to at least one of: a space emission pattern of the second ultraviolet source or a flow absorption distance dependence from the second ultraviolet source.

5. The system of claim 4, further comprising:
an inlet adjacent to the first portion, wherein the medium enters the shaped treatment chamber through the inlet and flows through the second portion away from the first portion; and
an outlet adjacent to the third portion, wherein the medium flows through the fourth portion towards the third portion and exits the shaped treatment chamber through the outlet.

6. The system of claim 1, wherein at least a portion of an interior of walls forming the shaped treatment chamber is coated with an agent, wherein the agent suppresses growth of a possible contaminant of the medium within the treatment chamber.

7. The system of claim 1, further comprising:
an outer treatment chamber encapsulating the shaped treatment chamber, wherein the medium first enters the outer treatment chamber and wherein at least a portion of at least one wall of the shaped treatment chamber is permeable to allow the medium to pass there through into the shaped treatment chamber; and
an outlet located within the shaped treatment chamber, wherein the medium exits the shaped treatment chamber and the outer treatment chamber via the outlet.

8. The system of claim 1, wherein an interior of walls forming the shaped treatment chamber comprise a directional reflectivity that varies based on a distance from the first ultraviolet source.

9. The system of claim 1, further comprising means for disturbing a flow of the medium through the shaped treatment chamber.

10. The system of claim 1, further comprising means for adding an agent to the medium within the shaped treatment chamber, wherein the agent treats at least one contaminant in the medium.

11. The system of claim 1, further comprising:
means for determining at least one of: a level of contamination of the medium or a type of contamination of the medium; and
means for operating at least one of: the first ultraviolet source, a flow rate of the medium through the shaped treatment chamber, or a source for adding an agent to the medium within the shaped treatment chamber based on the at least one of: the level of contamination of the medium or the type of contamination of the medium.

12. A system for treating a medium, the system comprising:
an ultraviolet treatment chamber through which the medium moves;
an ultraviolet source, wherein the ultraviolet source emits ultraviolet light into the ultraviolet treatment chamber;
an agent source, wherein the agent source introduces an agent for treating the medium within the ultraviolet treatment chamber; and
a computer system configured to implement a method of treating the medium by:
determining at least one of: a level of contamination of the medium or a type of contamination of the medium; and
operating the ultraviolet source and the agent source based on the at least one of: the level of contamination of the medium or the type of contamination of the medium to treat the medium in the ultraviolet treatment chamber by concurrently introducing the agent and emitting the ultraviolet light.

13. The system of claim 12, wherein the determining includes:
acquiring fluorescence data corresponding to the medium; and
correlating the fluorescence data with the at least one of: the level of contamination of the medium or the type of contamination of the medium.

14. The system of claim 12, wherein the ultraviolet treatment chamber comprises a shaped treatment chamber including:
a first portion from which ultraviolet light emitted by the ultraviolet source enters the shaped treatment chamber; and a second portion fluidly attached to the first portion, wherein an area of a cross-section of the second portion increases with distance from the first portion to approximately conform to at least one of: a space emission pattern of the ultraviolet source or a flow absorption distance dependence from the ultraviolet source.

15. The system of claim 12, further comprising:
an outer treatment chamber encapsulating the ultraviolet treatment chamber, wherein the medium first enters the outer treatment chamber and wherein at least a portion of at least one wall of the ultraviolet treatment chamber is permeable to allow the medium to pass there through into the ultraviolet treatment chamber; and
an outlet located within the ultraviolet treatment chamber, wherein the medium exits the ultraviolet treatment chamber and the outer treatment chamber via the outlet.

16. The system of claim 12, wherein at least a portion of the ultraviolet light emitted by the ultraviolet source activates the agent.

17. A system for treating a medium, the system comprising:
an ultraviolet treatment chamber;
an ultraviolet source, wherein the ultraviolet source emits ultraviolet light into the ultraviolet treatment chamber;
an outer treatment chamber encapsulating the ultraviolet treatment chamber, wherein the medium first enters the outer treatment chamber and wherein at least a portion of at least one wall of the ultraviolet treatment chamber is permeable to allow filtered medium to pass there through into the ultraviolet treatment chamber; and
an outlet located within the ultraviolet treatment chamber, wherein the medium exits the ultraviolet treatment chamber and the outer treatment chamber via the outlet.

18. The system of claim 17, wherein the ultraviolet treatment chamber comprises a shaped treatment chamber including:
a first portion from which ultraviolet light emitted by the ultraviolet source enters the shaped treatment chamber; and
a second portion fluidly attached to the first portion, wherein an area of a cross-section of the second portion increases with distance from the first portion to approximately conform to at least one of: a space emission pattern of the ultraviolet source or a flow absorption distance dependence from the ultraviolet source.

19. The system of claim 17, further comprising means for adding an agent to the medium within the shaped treatment chamber, wherein the agent treats at least one contaminant in the medium and wherein at least a portion of the ultraviolet light emitted by the ultraviolet source activates the agent.

20. The system of claim 17, further comprising:
means for determining at least one of: a level of contamination of the medium or a type of contamination of the medium; and
means for operating at least one of: the ultraviolet source, a flow rate of the medium through the system, or a source for adding an agent to the medium within the shaped treatment chamber based on the at least one of: the level of contamination of the medium or the type of contamination of the medium.

* * * * *